US00PP24733P3

(12) United States Plant Patent
Radler

(10) Patent No.: US PP24,733 P3
(45) Date of Patent: Aug. 5, 2014

(54) ***TRADESCANTIA* PLANT NAMED 'RADTRAD'**

(50) Latin Name: *Tradescantia virginiana*
Varietal Denomination: Radtrad

(71) Applicant: CP Delaware, Inc., Wilmington, DE (US)

(72) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 104 days.

(21) Appl. No.: 13/573,875

(22) Filed: Oct. 11, 2012

(65) Prior Publication Data

US 2014/0109272 P1 Apr. 17, 2014

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Annette Para
(74) *Attorney, Agent, or Firm* — Buchanan, Ingersoll & Rooney PC

(57) ABSTRACT

A new *Tradescantia* plant is provided that displays a spreading mounded growth habit. The new variety commonly flowers from June to November and forms in abundance large purple flowers in clusters on a substantially uniform basis. The plant propagates well through the use of cuttings. An additional choice is provided to gardeners seeking an herbaceous perennial. Attractive linear green leaves with substantially parallel venation are formed. The plant is well suited for providing colorful distinctive ornamentation.

2 Drawing Sheets

Botanical/commercial classification: *Tradescantia virginiana*/Spiderwort.

Varietal denomination: cv. Radtrad.

SUMMARY OF THE INVENTION

The new *Tradescantia virginiana* variety of the present invention is a member of the Commelinaceae family and was discovered during 2007 as a seedling growing in the garden of my home at Greenfield, Wis., U.S.A. among plants of the 'Little Doll' variety (non-patented in the United States). The female parent (i.e., seed parent) is believed to be the 'Little Doll' variety. The male parent (i.e., pollen parent) is unknown. Such presumed parentage of the new cultivar of the present invention can be expressed as follows:

'Little Doll'×Unknown.

The new variety of the present invention was carefully preserved and has been further studied and evaluated. Had the new variety of the present invention not been discovered and preserved it would have been lost to mankind.

It was found that the new *Tradescantia* plant of the present invention exhibits the following combination of characteristics:

(a) displays a spreading mounded growth habit,
(b) forms attractive linear green leaves with substantially parallel venation,
(c) forms in abundance large purple flowers in clusters on a substantially uniform basis,
(d) propagates readily through the use of cuttings, and
(e) is well suited for providing distinctive ornamentation.

The new cultivar of the present invention well meets the needs of the horticultural industry and expands the choice of herbaceous perennials. It is especially well suited for providing ornamentation in gardens and residential settings. The plant performs particularly well as a border planting, and when grown in containers. Attractive purple flowers commonly are abundantly formed from June to November. The growing requirements for the new cultivar are generally comparable to those of the species. The purple blossom coloration contrasts nicely with the green foliage.

The new variety can be readily distinguished from the 'Little Doll' variety by its larger plant size at maturity. More specifically, when grown outdoors in the ground, the 'Little Doll' commonly assumes a height of approximately 12 inches compared to a height of 18 inches for the new variety. Also, the 'Little Doll' variety commonly assumes a width of approximately 18 inches compared to a width of approximately 24 inches for the new variety.

The new variety also can be readily distinguished from the 'Bluestone' variety (non-patented in the United States) and the 'Concord Grape' variety (non-patented in the United States). More specifically, the new variety forms blossoms in greater abundance than the 'Bluestone' variety, and forms larger flower buds and larger more blue flower clusters than the 'Concord Grape' variety.

The use of node cuttings and division have been used to asexually propagate the new variety at West Grove, Pa., U.S.A. It has been found that the distinctive combination of characteristics of the new variety is firmly fixed and is reliably transmitted to succeeding generations following such asexual reproduction.

The new cultivar has been named 'Radtrad' and will be marketed under the AMETHYST KISS trademark.

BRIEF DESCRIPTION OF THE PHOTOGRAPHS

The accompanying photographs show typical mature specimens of the new variety in color as reasonably true as it is possible to make the same in an illustration of this character while growing outdoors in containers in full sun at West Grove, Pa., U.S.A. The photographs were obtained during April, 2009.

DETAILED DESCRIPTION

Figure 1:
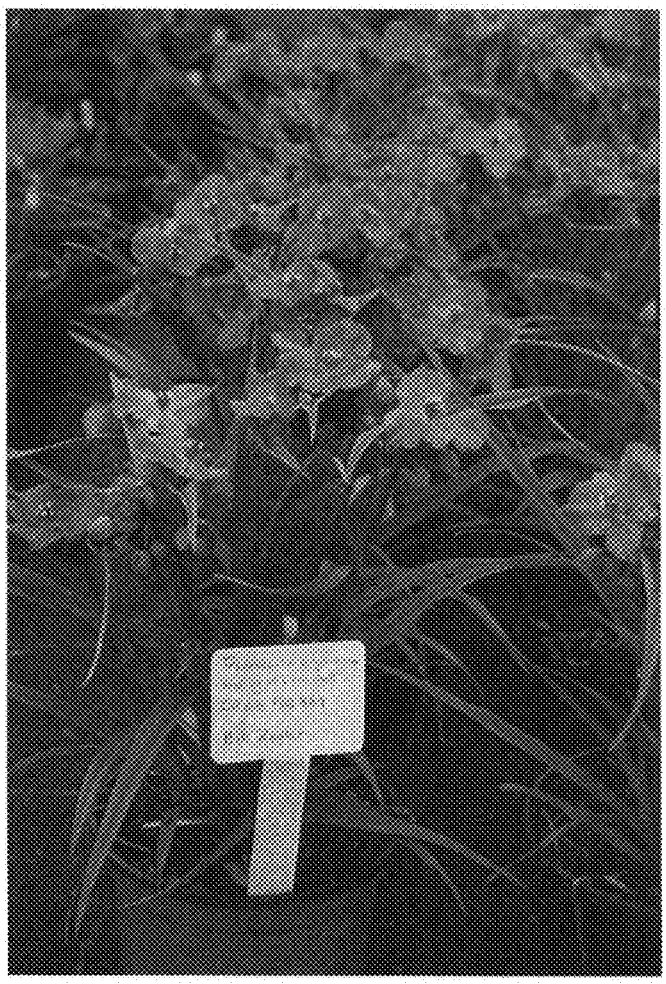
FIG. 1 illustrates an overall view of a typical flowering plant.
Figure 2:
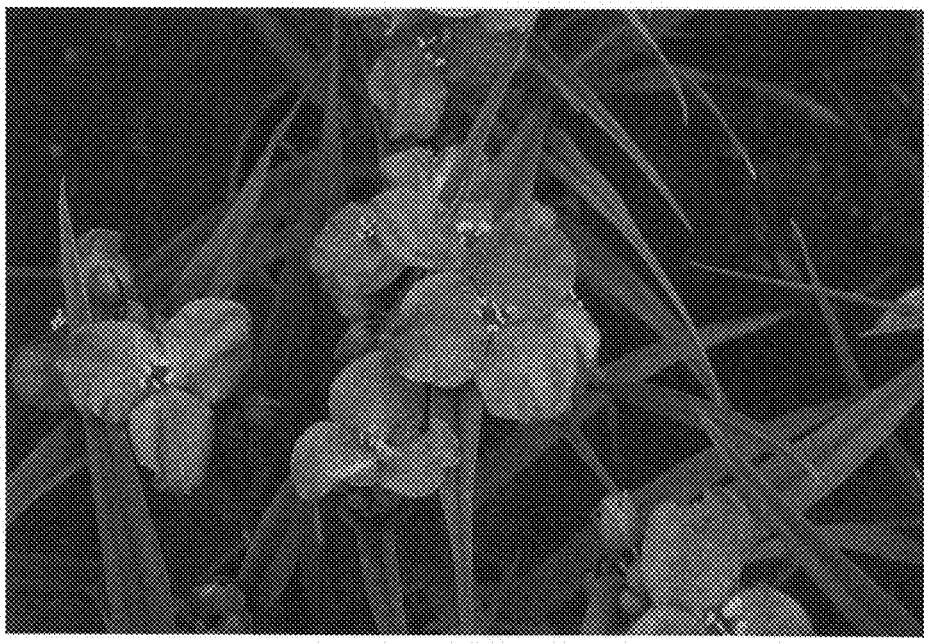
FIG. 2 illustrates a closer view of the typical attractive blossoms and foliage.

The following is a detailed description of the new cultivar that was obtained while observing plants during September 2011 when grown in containers outdoors at West Grove, Pa., U.S.A. The chart used in the identification color is The R.H.S. Colour Chart of The Royal Horticultural Society, London, England (1995 Edition or equivalent).

Botanical classification: *Tradescantia virginiana*, 'Radtrad'.

Plant:

*Habit*.—Spreading and mounded.

*Type*.—Herbaceous perennial.

*Height*.—Approximately 18 inches including flowers at maturity when in bloom.

*Width*.—Approximately 24 inches including flowers at maturity when in bloom.

Leaflets:

*Arrangement*.—Cauline, alternate.

*Shape*.—Linear, sometimes with inward folding at mid-vein.

*Length*.—Approximately 32 cm on average when mature.

*Width*.—Approximately 1 cm on average at widest point when mature.

*Margins*.—Entire.

*Apex*.—Acuminate.

*Base*.—Perfoliate.

*Texture*.—Glabrous.

*Venation*.—Substantially parallel to length.

*Petiole*.—Absent.

Inflorescence:

*Type*.—Terminal umbel-like cyme subtended by two bracts.

*Flowering season*.—June to November.

*Bracts*.—Shape: linear similar to leaves. Length: commonly approximately 10.1 cm on average. Width: commonly approximately 1.3 cm at the widest point. Color: near Green Group 137A on upper and under surfaces.

*Peduncle*.—Absent.

*Pedicels*.—Length: commonly approximately 1.5 cm on average. Diameter: commonly approximately 6 mm on average. Color: near Purple Group 78A.

*Buds*.—Shape: generally ovoid. Length: commonly approximately 1 cm on average. Diameter: commonly up to 6 mm prior to opening. Color: Yellow-Green Group 144A commonly with Violet-Blue Group 93B visible between sepals.

*Flower*.—Type: single, actinomorphic to irregular. Diameter: commonly approximately 3.5 cm on average when fully open. Shape: hypogynous with petals arranged in an orbicular configuration. Petal number: three. Petal length: commonly approximately 1.8 cm on average. Petal width: commonly approximately 2 cm on average. Petal margin: entire. Petal tip: generally obtuse. Petal base: attenuate. Petal texture: glabrous on upper and under surfaces. Petal color: near Violet-Blue Group 89C on the upper surface, and near Violet-Blue Group 89D on the under surface. Fragrance: none observed.

*Sepal number*.—Three or four per individual flower.

*Sepal shape*.—Lanceolate.

*Sepal texture*.—Short pubescence on outer surface.

*Sepal margin*.—Entire.

*Sepal apex*.—Acute.

*Sepal base*.—Truncate.

*Sepal length*.—Commonly approximately 1.2 cm on average.

*Sepal width*.—Commonly approximately 6 mm at widest point.

*Sepal color*.—When fully open near Yellow-Green Group 144B on the upper surface, and near Yellow-Green Group 144A on the under surface.

*Stamen number*.—Six per flower.

*Filament length*.—Approximately 8 mm on average.

*Filament color*.—Violet-Blue Group 89C.

*Filament texture*.—Commonly covered with fine hairs below anther.

*Anther shape*.—Reniform.

*Anther length*.—Approximately 1 mm on average.

*Anther color*.—Near Yellow-Orange Group 14A.

*Pollen quantity*.—Abundant.

*Pollen color*.—Yellow-Orange Group 14A.

*Pistil number*.—One per flower.

*Pistil length*.—Approximately 8 mm on average.

*Style length*.—Approximately 6 mm on average.

*Style color*.—Near Violet-Blue Group 89C.

*Stigma color*.—Near Yellow-White Group 145C.

*Ovary size*.—Commonly approximately 2 mm in length.

*Fruit and seeds*.—None observed.

Development:

*Blooming*.—Commonly during June to November.

*Resistance to diseases*.—Believed to be typical of the genus during observations to date.

*Resistance to pests*.—Believed to be typical of the genus during observations to date.

*Hardiness*.—Hardy in U.S.D.A. Hardiness Zone Nos. 5 to 10.

Plants of the 'Radtrad' variety have not been observed under all possible environmental conditions to date. Accordingly, it is possible that the phenotypic expression may vary somewhat with changes in light intensity and duration, cultural practices, and other environmental conditions.

I claim:

1. A new and distinct *Tradescantia* plant that exhibits the following combination of characteristics:

(a) displays a spreading mounded growth habit, (b) forms attractive linear green leaves with substantially parallel venation, (c) forms in abundance large purple flowers in clusters on a substantially uniform basis, (d) propagates readily through the use of cuttings, and (e) is well suited for providing distinctive ornamentation; substantially as illustrated and described.

* * * * *